United States Patent [19]

Pühler et al.

[11] Patent Number: 4,673,642
[45] Date of Patent: Jun. 16, 1987

[54] PLASMID P SVH 1 AND ITS USE

[75] Inventors: Alfred Pühler; Wolfgang Wolleben, both of Bielefeld; Michael Leineweber, Hofheim am Tanus, all of Fed. Rep. of Germany

[73] Assignee: Hoechst Aktiengesellschaft, Frankfurt, Fed. Rep. of Germany

[21] Appl. No.: 642,742

[22] Filed: Aug. 20, 1984

Related U.S. Application Data

[63] Continuation of Ser. No. 398,895, Jul. 16, 1982, abandoned.

[30] Foreign Application Priority Data

Jul. 20, 1981 [DE] Fed. Rep. of Germany ....... 3128669

[51] Int. Cl.[4] .................. C12P 19/34; C12P 21/00; C12N 15/00; C12N 1/20; C12N 1/00; C12R 1/465; C12R 1/61
[52] U.S. Cl. ........................................ 435/91; 435/68; 435/172.3; 435/253; 435/317; 435/886; 435/906; 435/29; 435/75
[58] Field of Search .................. 435/68, 70, 91, 172.3, 435/253, 317, 886, 906; 935/75, 29

[56] References Cited

U.S. PATENT DOCUMENTS

| 4,273,875 | 6/1981 | Manis | 435/91 |
| 4,332,900 | 6/1982 | Manis et al. | 435/91 |
| 4,338,400 | 7/1982 | Manis et al. | 435/172 |
| 4,340,674 | 7/1982 | Manis et al. | 435/172 |
| 4,343,906 | 8/1982 | Reusser et al. | 435/253 |
| 4,360,597 | 11/1982 | Bibb et al. | 435/172 |
| 4,401,761 | 8/1983 | Manis et al. | 435/68 |

OTHER PUBLICATIONS

Akagawa et al.: Chem. Abstr. 84:14569p (1976) of J. Gen. Microbiol. 90, Pt. 2, 336 (1975).
Helling et al., "The Molecular Cloning of Genes—General Procedures", in *Genetic Engineering*, Chakrabarty (ed.), 1978, CRC Press, Inc., Boca Raton, Fla., pp. 1, 17 and 18.
Malik et al., Plasmid 2, 627–631 (1979).
Okanishi et al., J. Antibiotics 33, 88–91 (1980).
Chem. Abstr. 92, 72493k (1980) Hayakawa et al.

*Primary Examiner*—James Martinell
*Attorney, Agent, or Firm*—Curtis, Morris & Safford

[57] ABSTRACT

The plasmid p SVH 1, which is obtained from *Streptomyces venezuelae* DSM 40755 and which has a molecular weight of 8.4 megadaltons, a contour length of 4.1 μm and a molecular size of 12.6 kilobases, and its use for the construction of a vector and for cloning foreign DNA in suitable host organisms.

2 Claims, 1 Drawing Figure

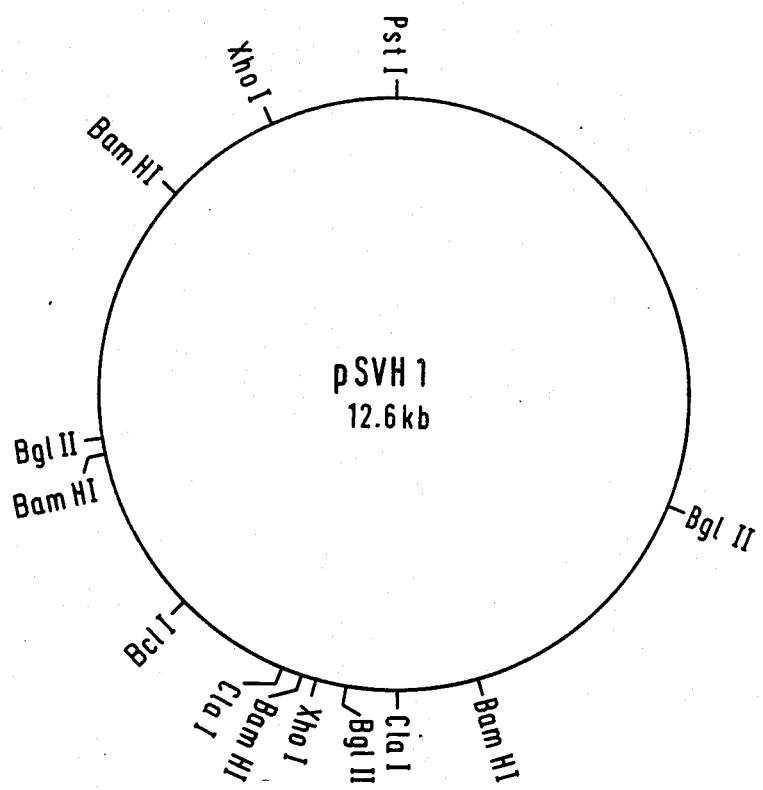

PLASMID P SVH 1 AND ITS USE

This application is a continuation of application Ser. No. 398,895, filed July 16, 1982, now abandoned.

The invention relates to the plasmid p SVH 1 and its use for the preparation of a hybrid vector by which the DNA of Streptomycetes can be transferred to other microorganisms, in particular to other species of Streptomycetes.

It is known from German Offenlegungsschrift No. 3,005,226 that the plasmid pUC 6 can be obtained from a culture of *Streptomyces espinosus*. It is furthermore known from the PCT Application 79/01169 that a plasmid, which appears to be suitable as a vector for the introduction of DNA into some species of Streptomyces, can be obtained from *Streptomyces lividans*.

From these facts, it can be seen that particular importance is attributed to the application of genetic engineering methods to species of Streptomyces forming antibiotics. However, most of the plasmids known hitherto have remained of little interest for practical application, since, on the one hand, they cannot easily be prepared in relatively large amounts. On the other hand, for genetic engineering purposes, it is very important to have plasmids available which are present in many copies per cell (=multicopy plasmids), if they are to find reasonable application as vectors for the amplification of cloned genes.

The genetic improvement of the strains of Streptomycetes used for the preparation of antibiotics with the object of increasing the amount of antibiotics formed is an important aim. However, it can only be successfully achieved with genetic engineering methods if a plasmid is available which is not immediately eliminated again from the species of Streptomyces employed as the host cell, as is frequently observed for species which are not related to one another.

Thus the aim was to find a multicopy plasmid which is easily isolable and stable in the cell and which is suitable for the genetic improvement of Streptomyces strains. It is obvious that this aim may most easily be achieved if it is possible to identify a suitable plasmid in another species of Streptomyces.

It has now emerged that this aim is achieved by the plasmid p SVH 1, which is obtained from a culture of *Streptomyces venezuelae* DSM 40 755, and which has a molecular weight of 8.4 megadaltons, a contour length of 4.1 μm and comprises 12.6 kilobases (=kb).

The novel plasmid was deposited under the taxonomic designation "*Streptomyces venezuelae*" in the Deutsche Sammlung von Mikroorganismen, Griesebachstrass 8, Goettingen, Federal Republic of Germany, under the terms of the Budapest Treaty, on Oct. 1, 1981, and has been assigned accession No. DSM 40755.

The strain of *Streptomyces venezuelae* used for this purpose is described in detail by L. Ettlinger, R. Corbatz and R. Hütter, Arch. Mikrobiol. 31, 326–358 (1958), particularly from page 352 onwards. A further description is to be found in R. Hütter "Systematik der Streptomyceten" ("Systematics of Streptomycetes"), Karger-Verlag, Basel/New York, 1967, page 60.

*Streptomyces venezuelae* DSM 40755 is regarded as an outstanding provider of plasmids particularly because in this instance in each cell there are many more than 20 plasmids present, which are particularly well suited for carrying out genetic engineering tasks due to their low molecular weight of 8.4 megadaltons.

The isolation of the plasmids from *Streptomyces venezuelae* DSM 40755 is carried out by processes known per se. The strain is initially cultured in a suitable medium containing glycine. After harvesting, washing and homogenizing the mycelium, the cell walls are removed with lysozyme. After treating the cells with proteinase K and sodium dodecyl sulfate, the cells lyse so that cell residues and chromosomal DNA can then be separated off by centrifugation. Thereafter, the plasmids are precipitated with polyethylene glycol and worked up by a process described by H. C. Birnboim and J. Doly, J. Nucl. Acids Res. 7, 1513–1523 (1975) for subsequent rapid investigations. The plasmid p SVH 1 thus enriched can be employed directly for analytical investigations and subjected to treatment with restriction endonucleases. A pure preparation can be obtained by two consecutive cesium chloride density gradient centrifugations.

The plasmid p SVH 1 thus obtained can be characterized on agarose gels by endonucleolytic cleavage with restriction enzymes. By this means, the number and size of the particular p SVH 1 fragments can be determined. It is characteristic of the plasmid p SVH 1 that it has no cleavage sites for the restriction endonucleases Eco R I, Hind III, Xba 1 and Hpa 1, is only cleaved once by the restriction endonucleases Pst I and Bcl I, and is cleaved by Xho I into two fragments of lengths 7.6 and 4.9 kb, by Cla I into two fragments with lengths 11.8 and 0.8 kb, by Bgl II into three fragments with lengths 7.5, 2.8 and 2.4 kb and by Bam H I into four fragments with lengths 7.7, 2.0, 1.8 and 1.2 kb. In addition, the cleavage sites of some of these enzymes have been related to one another on the circular plasmid molecule (see attached figure). Furthermore, 4 fragments are produced by endonucleolytic cleavage with Pvu II and Kpn I, 5 with Nru I, Pvu I and Sma I, 7 with Sst II and Sac II, 8 with Sst I and many more than 10 with Sal I.

Contour measurements on a large number of plasmids produced a size of 4.1 μm and a molecular weight of 8.23 megadaltons derived therefrom. This value is in good agreement with molecular weights calculated by the addition of the weights of restriction fragments after separation by gel electrophoresis (=8.4 megadaltons). Identical or similar plasmids have not hitherto been found in any other *Streptomyces venezuelae* biotype [cf. V. S. Malik and F. Reuser, Plasmid 2, 627–31 (1979)].

The plasmid p SVH 1 is very suitable for the preparation of a vector for several reasons. Above all, the extremely high copy number of much more than 20 plasmids per cell and its stability are very important prerequisites for the use of p SVH 1 for genetic engineering tasks. Hitherto, plasmid-free strains of *Streptomyces venezuelae* DSM 40755 have not been observed in spite of extensive investigations. On plasmid isolation, yields of more than 200 μg, calculated from one liter of original culture of Streptomycetes, were always achieved.

The plasmid p SVH 1 is above all suitable for the formation of a hybrid vector which can be introduced into other species of Streptomycetes. This is because it has been found that all the plasmids hitherto known can only be established in relatively few host cells. Thus, it is known, for example that there are barriers to the multiplication of foreign DNA between Gram-positive and Gram-negative bacteria (cf. P. Courvalin and M. Fiandt, Gene 8, 247–269 (1980)). The greatest chances of successful cloning always exist when the hybrid vector is introduced into a closely related host cell. All the data hitherto published on Streptomycetes plasmids and phages even indicate that stable introduction is only possible into a very limited number of other Streptomycetes. Cloning of Streptomycetes DNA in Streptomycetes will always be necessary when quite a large number of genes, and not only one or a few genes, are to be cloned, which, for example, are involved in the synthesis of an antibiotic.

Cloning the genes for a complete metabolic pathway represents, at the very least, a vast amount of work, even if it does not become a virtually insoluble problem, perhaps due to distribution of the genes over the entire Streptomycetes genome. In a Streptomycetes cloning system, under certain circumstances in such cases, for example when a bottleneck in metabolism is present, the amplification of a single gene can suffice to obtain significantly higher yields. Equally, for producing hybrid antibiotics, as may be envisaged by combination of closely related metabolic pathways—for example by insertion of an enzyme modifying an antibiotic—only a Streptomycetes host vector system gives promise of success for the same reason. The plasmid p SVH 1 is, for these reasons, outstandingly suitable for the preparation of a hybrid vector in order to make an increase in the yield of antibiotics possible.

The same genetic engineering methods are used for the preparation of the hybrid vector as have previously been employed already for *Escherichia coli* plasmids and have also been used for Streptomycetes by M. Bibb, J. C. Schottel, S. N. cohen, Nature 284, 526-531 (1980), and C. J. Thompson, J. M. Ward, D. A. Hopwood, Nature 286 525-527 (1980).

By these known processes, not only genes which carry antibiotic resistance can be inserted into the plasmid p SVH 1 in some of the cleavage sites obtained with the abovementioned restriction endonucleases, but also genes which bring about an increase in antibiotic production. The hybrid plasmids thus obtained are, according to all the experimental results obtained hitherto, just as viable and capable of reproduction in Streptomyces cells as the initial plasmid.

The invention is further illustrated by the following example, in which data in percent relate to weight unless otherwise specified.

Example

1. Culture and formation of protoplasts of *Streptomyces venezuelae* DSM 40755

Culture was carried out in suitable vessels, for example 300 ml conical flasks, in 50 ml of medium, for example Luria broth or 2 YT (cf. J. H. Miller, Experiments in Molecular Genetics, Cold Spring Harbor Laboratory, 1972) or in other media with a utilizable source of nitrogen and carbon. All media additionally contained 0.5% by weight of glycine. Inoculation was either done with a spore suspension or a loop full of spores. Incubation was carried out at 32° C. in a shaking machine, amplitude 4 cm, at 220 rpm for 2–3 days up to the early stationary phase. Then the cells were harvested by centrifugation at 6000×g and 4° C. for 10 minutes. For the formation of protoplasts for subsequent transformation with plasmids, this and the following steps were carried out under sterile conditions. The mycelium pellet was washed once with water and then taken up in 5 ml of suitable hypertonic buffer, for example consisting of 25% sucrose, 50 mM ethylenediaminetetraacetic acid (=EDTA) and 50 mM trishydroxymethylaminomethane (tris) at pH 8. Then the mycelium was ruptured by two to four strokes in a glass homogenizer. This facilitates the approach of the lysozyme to its site of action. After the addition of 1 ml of lysozyme (containing 10 mg/ml in 50 mM tris at pH 8), digestion at room temperature for 60 minutes is sufficient to achieve virtually complete formation of protoplasts.

2. Lysis of the cells

For the preparation of plasmid DNA, the protoplasts were treated further for half an hour at room temperature with one milliliter of proteinase K (containing 1 mg/ml in 50 mM tris at pH 8). Then the cell suspensions were treated with sodium dodecyl sulfate to give a final concentration of 0.1% and then incubated a further half hour at room temperature. Then 7 ml of a solution of 2 mM EDTA, 2M sodium chloride, 50 mM tris at pH 8 were added and the highly viscous mixture was incubated on ice for at least one hour. Cell residues and the major amount of the chromosomal DNA were then centrifuged off by centrifugation at 20,000×g and 4° C. for one hour and worked up under various conditions, depending on whether an analytical or a preparative plasmid isolation was intended.

3. (a) Analytical plasmid isolation

The supernatant from the centrifugation was carefully poured off and the plasmid DNA precipitated out by the addition of polyethylene glycol 6000 up to a final concentration of 10%. After incubation on ice for one hour, the precipitate was collected by centrifugation at 20,000×g and 4° C. for 20 minutes, the pellet was taken up in 500 µl of 0.2N NaOH and incubated at 0° C. for half an hour. Then the alkaline suspension was neutralized by the addition of 375 µl of 3 molar sodium acetate solution of pH 4.8. By this means, the chromosomal DNA, which had been partially denatured to single strands by the treatment with alkali, was converted again in regions of partial homology to double stranded DNA, and a product with a huge molecular weight was formed by crosslinking of the chromosomal DNA fragments, and this can easily be removed by centrifugation n at 1,500×g and 4° C. for 5 minutes [cf. H. C. Birnboim and J. Doly, Nucleic Acids Research 7, 1513-23 (1979)]. The supernatant was then treated with 2.5 times the volume of ethanol and, after incubation at −18° C. for 4 hours, the precipitated plasmid DNA was collected by centrifugation (15,000×g, 4° C., 20 minutes) and washed once with 78% strength ethanol. The enriched plasmid DNA can then be taken up in 0.1 mM EDTA, 20 mM tris at pH 8 and used for the rapid analysis of the plasmid with restriction enzymes.

(b) Preparative plasmid isolation

After the polyethylene glycol precipitation which has already been described for the analytical plasmid isolation, the plasmid DNA collected by centrifugation at 20,000×g and 4° C. for 20 minutes was taken up in 6 ml of 10 mM EDTA, 50 mM tris at pH 8. The volume of the suspension obtained was measured with a pipette and 1 g of cesium chloride was added per milliliter of suspension. Then 200 µl of ethidium bromide (10 mg/ml) were added and the suspension was centrifuged in an ultracentrifuge at 80,000×g and 15° C. for 60 hours. The more dense band was visualized with UV light, drawn off by lateral aspiration with an injection needle and again treated with 5 ml of a solution of 10 mM EDTA, 50 mM tris of pH 8 which additionally contains 5 g of cesium chloride. Recentrifugation in the ultracentrifuge was carried out under the same conditions as was the subsequent isolation of the band. The collected DNA was then extracted several times with n-butanol saturated with cesium chloride to remove ethidium bromide and the aqueous phase was dialyzed against 10 mM EDTA, 50 mM tris at pH 8 for at least 6 hours. The dialyzate was then treated with 2½ times the volume of ethanol and, after 4 hours at −18° C., precipitated plasmid DNA could be pelleted by centrifugation at 15,000×g and 4° C. for 20 minutes. The precipitate was then washed once with 78% strength ethanol and stored in 0.1 mM EDTA, 20 mM tris at pH 8 and 4° C.

4. Characterization of plasmid DNA

Investigation by electron microscopy was by standard procedures [A. K. Kleinschmidt, Monolayer Techniques, in Electron Microscopy of Nucleic Acid Molecules, in Methods of Enzymology, S. P. Colowick and N. O. Caplan, Academic Press, volume 25, 361–377 (1968)]. By this means, the contour length was determined to be 4.1 μm. From the contour length of the plasmid, a molecular weight of 8.4 megadaltons could be determined. The characterization of the plasmid p SVH 1 was carried out with a large number of various restriction enzymes. The digested DNA was then separated by electrophoresis on 0.7% strength horizontal agarose gels (2 mM EDTA, 40 mM sodium acetate, 80 mM tris, pH 8.3) in a voltage gradient of 5 V/cm for 4 hours. In addition, the molecular weights of the unknown fragments could be determined using marker fragments of known size subjected to electrophoresis on the same gel by comparison of the migration distances in the electric field. The cleavage sites of 6 restriction enzymes were exactly related to one another on the circular p SVH 1 molecule (cf. the attached figure).

The single Pst I cleavage site on the plasmid was arbitrarily taken as the zero point for this purpose. The position of the cleavage site of an enzyme, for example that of Bam H I, on fragments as produced by treatment with another restriction endonuclease was determined by two successive digestions. After restriction with the enzyme Bam H I, an aliquot was applied directly to the gel and another aliquot was extracted twice with phenol which was saturated with 100 mM tris buffer, pH 8, and the aqueous phase was extracted three times with ether to remove the phenol. Then the DNA was precipitated with 2½ times the volume of ethanol and could then, suspended in the digestion buffer, be exposed to the action of the second enzyme. The doubly digested DNA was then applied to the gel together with a plasmid sample which had only been treated with the second enzyme. By this means, the fragment on which the second enzyme has a restriction site can be determined.

The number of copies of p SVH 1 with significantly more than 20 copies per cell was determined in the following manner: carbon-14-labeled thymidine molecules, which are incorporated in the cell to the same extent in the chromosomal and in the plasmid DNA, were made available to the cells of *Streptomyces venezuelae* DSM 40755 in shaken culture. After lysis of the cells and separation off of the crude lysates, without previous separation off of the chromosomal DNA, by means of cesium chloride density gradients in the presence of ethidium bromide, the gradient was then divided into about 50 fractions and the radioactivity of the individual fractions was determined. From the ratio of activity of the denser plasmid and the lighter chromosomal bands and knowing the molecular weights of the plasmid and the estimated molecular weight of the chromosome, the number of copies of the plasmid per cell could be calculated [cf. R. Radloff, W. Bauer and J. Vinograd, Proc. Nat. Acad. Sci. U.S., 57, 1514–1520 (1967)].

TRANSFORMATION OF STREPTOMYCETES WITH THE PLASMID P SVH 1

The transformation system developed by Hopwood and coworkers was used [M. J. Bibb, J. M. Ward and D. A. Hopwood, Nature 274, 398–400 (1978)]. The protoplasts were prepared as described under (1.) and centrifuged off (6,000×g, 4° C., 5 minutes) and taken up in a protoplast medium (25% sucrose, 1.5 mM K$_2$SO$_4$, 10 mM MgCl$_2$, 0.36 mM KH$_2$PO$_4$, 25 mM CaCl$_2$, 25 mM NaCl, 25 mM tris, pH 7.2).

After incubation at 4° C. for 30 minutes, the protoplasts were again pelleted and the pellet was suspended in 1 ml of fresh protoplast medium by careful aspiration into and ejection from a pipette. Then the plasmid p SVH 1 was added and the suspension was treated with 3 ml of 30% strength polyethylene glycol 1000, mixed and incubated at 0° C. for a further 4 minutes. Then 8 ml of protoplast medium were added and the suspension obtained was again centrifuged down. The pellet was then covered with a modified regeneration medium (25% sucrose, 30% glucose, 1.5 mM K$_2$SO$_4$, 10 mM MgCl$_2$, 0.1% casaminoacids, 0.5% yeast extract, 0.36 mM KH$_2$PO$_4$, 20 mM CaCl$_2$, 0.3 mM L-proline, 25 mM NaCl, 25 mM tris, pH 7.2) and incubated at 37° C. in a shaking water-bath for 2 hours. For isolating the individual colonies, the cell suspension produced was then plated out on agar plates containing suitable selective media and transformates could be analyzed by the rapid dissolution process described under 3 (a) and the plasmid DNA contained therein could be characterized with restriction enzymes.

6. Cloning foreign DNA in the plasmid p SVH 1

The plasmid p SVH 1 was opened with a restriction enzyme. At the same time, a chromosomal DNA to be built into the plasmid was cleaved such that cleavage sites with the same ends, i.e. such as can be ligated together, were produced. After heating to 70° C. for 3 minutes, the two preparations were mixed, extracted with phenol and precipitated with ethanol as described under (4.). Subsequently, the DNA was taken up in ligase buffer (according to the manufacturer's instructions), treated with T4-DNA ligase and incubated for one hour at 16° C. and overnight with gradual cooling down to 4° C. The plasmid ligated in this manner was then introduced into a suitable Streptomycetes as described under (5.).

APPENDIX

The references cited on page 3, lines 20 to 25 refer, in turn, to J. Ehrlich, D. Gottlieb, P. R. Burkholder, L. E. Anderson and T. G. Pridham, Journal of Bacteriology, Vol. 56 (1948), 467–477. In this paper entitled "*Streptomyces Venezuelae*, n.Sp., the Source of Chloromycetin" details about morphology and physiology are given.

We claim:

1. Biologically pure plasmid pSVH 1, obtainable from a culture of *Streptomyces venezuelae* DSM 40755, which plasmid has a molecular weight of 8.4 megadaltons, a contour length of 4.1 microns, a molecular size of 12.6 kilobases, is not cleaved by the restriction endonucleases EcoR I, Hind III, Hpa I, and Xba I, is cleaved only once by Pst I and Bcl I, is cleaved by Xho I into two fragments 7.6 and 4.9 kilobases in length, is cleaved by Cla I into two fragments 11.8 and 0.8 kilobases in length, is cleaved by Bgl II into three fragments 7.5, 2.8, and 2.4 kilobases in length, and is cleaved by BamH I into four fragments 7.7, 2.0, 1.8, and 1.2 kilobases in length.

2. A method for constructing a vector and cloning foreign DNA in a suitable host organism, which method comprises cleaving the plasmid pSVH 1, combining said plasmid with foreign DNA to create said vector, and then transforming a Streptomycetes strain with said vector.

* * * * *

UNITED STATES PATENT AND TRADEMARK OFFICE
CERTIFICATE OF CORRECTION

PATENT NO. : 4,673,642
DATED : June 16, 1987
INVENTOR(S) : Puehler et al.

It is certified that error appears in the above-identified patent and that said Letters Patent is hereby corrected as shown below:

On the Title Page, in the section "[75] Inventors" change
   "Wolleben" to --Wohlleben-- and
   "Tanus" to --Taunus--, Signed and Sealed this Twenty-sixth Day of December, 1989

Attest:

JEFFREY M. SAMUELS

*Attesting Officer*          Acting Commissioner of Patents and Trademarks